US008344333B2

(12) United States Patent
Lu et al.

(10) Patent No.: US 8,344,333 B2
(45) Date of Patent: Jan. 1, 2013

(54) MULTI-COLOR FLUORESCENCE ENHANCEMENT FROM A PHOTONIC CRYSTAL SURFACE

(75) Inventors: Meng Lu, Champaign, IL (US); Stephen C. Shulz, Lee, NH (US); Brian T. Cunningham, Champaign, IL (US); Anusha Pokhriyal, Champaign, IL (US)

(73) Assignees: The Board of Trustees of the University of Illinois, Urbana, IL (US); SRU Biosystems, Inc., Woburn, MA (US)

( * ) Notice: Subject to any disclaimer, the term of this patent is extended or adjusted under 35 U.S.C. 154(b) by 13 days.

(21) Appl. No.: 13/135,246

(22) Filed: Jun. 28, 2011

(65) Prior Publication Data

US 2012/0007000 A1  Jan. 12, 2012

Related U.S. Application Data

(60) Provisional application No. 61/399,274, filed on Jul. 8, 2010.

(51) Int. Cl.
*G01N 21/64* (2006.01)
(52) U.S. Cl. .................................................. 250/458.1
(58) Field of Classification Search .............. 250/458.1
See application file for complete search history.

(56) References Cited

U.S. PATENT DOCUMENTS

| | | | |
|---|---|---|---|
| 5,006,716 A | 4/1991 | Hall | 250/458.1 |
| 6,437,345 B1 | 8/2002 | Bruno-Raimondi et al. | 250/458.1 |
| 7,708,945 B1 | 5/2010 | Abel et al. | 422/58 |
| 2006/0216204 A1 | 9/2006 | Budach et al. | 422/82.08 |
| 2008/0278722 A1 | 11/2008 | Cunningham et al. | 356/317 |
| 2009/0045351 A1 | 2/2009 | Smolyaninov et al. | 250/458.1 |

FOREIGN PATENT DOCUMENTS

| | | |
|---|---|---|
| EP | 1 085 315 | 3/2001 |
| WO | WO2008/156550 | 12/2008 |

OTHER PUBLICATIONS

Zhang et al., "High sensitivity photonic crystal biosensor incorporating nanorod structures for enhanced surface area," 2008, Sensors and Actuators B, vol. 131, pp. 279-284.*

(Continued)

*Primary Examiner* — Kiho Kim
(74) *Attorney, Agent, or Firm* — McDonnell Boehnen Hulbert & Berghoff LLP

(57) ABSTRACT

A photonic crystal substrate exhibiting resonant enhancement of multiple fluorophores has been demonstrated. The device, which can be fabricated uniformly from plastic materials over a ~3×5 in$^2$ surface area by nanoreplica molding, features a 1-D periodic grating structure which utilizes two distinct resonant modes to enhance electric field stimulation of a first dye excited by a first laser (e.g., $\lambda$=632.8 nm laser exciting cyanine-5) and a second dye excited by a second laser (e.g., $\lambda$=532 nm laser exciting cyanine-3). The first and second lasers could be replaced by a single variable wavelength (tunable) laser. Resonant coupling of the laser excitation to the photonic crystal surface is obtained for each wavelength at a distinct incident angle $\theta$. The photonic crystal is capable of amplifying the output of any fluorescent dye with an excitation wavelength in a given wavelength range (e.g., the range 532 nm<$\lambda$<660 nm) by selection of an appropriate incident angle. The device can be used for biological assays that utilize multiple fluorescent dyes within a single imaged area, such as gene expression microarrays.

25 Claims, 4 Drawing Sheets

OTHER PUBLICATIONS

PCT Search Report and Written Opinion in PCT/US2011/001155 dated Nov. 30, 2011.

Geddes, C.D. and J.R. Lakowicz, *Metal-Enhanced Fluorescence*. Journal of Fluorescence, 2002. 12(2): p. 121-129.

Moal, E.L., et al., *Enhanced fluorescence cell imaging with metal-coated slides*. Biophysical Journal, 2007. 92: p. 2150-2161.

Estrada, L.C., et al., *Small volume excitation and enhancement of dye fluorescence on a 2D photonic crystal surface*. Optics Express, 2010. 18(4): p. 3693-3698.

Wu, H.-Y., et al., *Magnification of photonic crystal fluorescence enhancement via TM resonance excitation and TE resonance extraction on a dielectric nanorod surface*. Nanotechnology, 2010. 21: p. 7.

Kinkhabwala, A., et al., *Large single-molecule fluorescence enhancements produced by a bowtie nanoantenna*. Nature Photonics, 2009. 3: p. 4.

Fan, S. and J.D. Joannopoulos, *Analysis of guided resonances in photonic crystal slabs*. Physical Review B, 2002. 65: p. 235112.

Willets, K.A. and R.P.V. Duyne, *Localized Surface Plasmon Resonance Spectroscopy and Sensing*. Annual Review of Physical Chemistry, 2006. 58: p. 30.

Anger, P., P. Bharadwaj, and L. Novotny, *Enhancement and Quenching of Single-Molecule Fluorescence*. Physical Review Letter, 2006. 96(11): p. 4.

Ganesh, N., et al., *Leaky-mode assisted fluorescence extraction: application to fluorescence enhancement biosensors*. Optics Express, 2008. 16(26): p. 21626-21640.

Mathias, P.C., et al., *Graded Wavelength One-Dimensional Photonic Crystal Reveals Spectral Characteristics of Enhanced Fluorescence*. Journal of Applied Physics, 2008. 103: p. 094320.

Mathias, P.C., H.-Y. Wu, and B.T. Cunningham, *Employing two distinct photonic crystal resonances for improved fluorescence enhancement*. Applied Physics Letters, 2009. 95(2): p. 3.

Budach, W., et al., *Generation of transducers for fluorescence-based microarrays with enhanced sensitivity and their application for gene expression profiling*. Analytical Chemistry, 2003. 75: p. 2571-2577.

Che, D., Y. Bao, and U.R. Mueller, *Novel surface and multicolor charge coupled device-based fluorescent imaging system for DNA microarrays*. Journal of Biomedical Optics, 2001. 6(4): p. 450-456.

Ganesh, N. and B.T. Cunningham, *Photonic Crystal Near UV Reflectance Filters Fabricated by Nano Replica Molding*. Applied Physics Letters, 2006. 88(7): p. 071110-071113.

Block, I.D., L.L. Chan, and B.T. Cunningham, *Large-Area submicron replica molding of porous low-k dielectric films and application to photonic crystal biosensor fabrication*. Microelectronic Engineering, 2007. 84(4): p. 603-608.

Ganesh, N., et al., *Enhanced fluorescence emission from quantum dots on a photonic crystal surface*. Nature Nanotechnology, 2007. 2: p. 515-520.

Lakowicz, J.R., *Radiative Decay Engineering: Biophysical and Biomedical Applications*. Analytical Biochemistry, 2001. 298: p. 1-24.

\* cited by examiner

US 8,344,333 B2

MULTI-COLOR FLUORESCENCE ENHANCEMENT FROM A PHOTONIC CRYSTAL SURFACE

PRIORITY

This application claims priority under 35 U.S.C. §119 to U.S. Provisional application Ser. No. 61/399,274 filed Jul. 8, 2010, the content of which is incorporated by reference herein.

STATEMENT REGARDING FEDERALLY SPONSORED RESEARCH OR DEVELOPMENT

This invention was made in part with federal funding provided by the National Institutes of Health and the National Science Foundation. The U.S. Government may have certain rights to the invention.

BACKGROUND

Fluorescence is one of the most sensitive detection and imaging tools available for life science research and diagnostic assays, [1] representing the most common method for determining the presence and concentration of analytes in a wide range of applications including DNA sequencing, DNA microarrays, immunoassays, and cell imaging. The ability to detect weak signals is essential for assays requiring the detection of analytes at low concentration. To address this challenge, researchers have developed many methods to enhance fluorescence emission, thereby improving detection sensitivity. A variety of nano-patterned surfaces have been studied for the purpose of enhancing fluorescence output [2-6]. Field enhancement in these structures arises from several effects which include locally intense optical fields, reduced fluorescence lifetimes, and directional emission [7-10].

Photonic crystal (PC) surfaces comprised of a periodic surface grating coated with a high refractive index dielectric have been demonstrated for fluorescence emission enhancement applications [11] through the use of narrowband resonant modes at specific wavelengths. PC-enhanced fluorescence (PCEF) takes advantage of the resonant evanescent field that has an increased local energy density compared to the excitation light source. The intensified evanescent field strongly excites fluorophores located within an evanescent decay length of the sensor surface, resulting in enhanced emission. Previous publications have demonstrated the use of PCEF with the resonant mode spectrally overlapping the laser wavelength, to excite fluorescent dyes [12] and, that at normal incidence illumination, a PC with a resonant mode at $\lambda$=632.8 nm can produce a 60-fold magnification of cyanine-5 (Cy-5) signal compared to an ordinary glass substrate [13].

Many biological fluorescence assays, such as gene expression microarrays [14-15], have been developed using multiple fluorescent dyes within a single imaged area. In order to enhance the emission from multiple fluorescent dyes, the PC surface must be designed with resonant wavelengths coinciding with the wavelength of multiple lasers that are used to excite the target fluorophores. The PC structure intrinsically supports resonant modes in a wavelength range as wide as 200 nm [16] because each wavelength couples resonantly with the structure for a distinct angle of incidence.

Further art of interest include the published patent applications U.S. 2008/0278722 and U.S. 2006/0216204 and PCT publication WO 2008/156550.

SUMMARY

Photonic crystal sensors are disclosed which include a single grating period (1-D periodic grating structure) which can resonantly couple light from multiple excitation lasers—each at a distinct incident angle—producing enhanced fluorescence for multiple dyes applied to the surface of the sensor. The grating structure is designed with grating depth and period to exhibit resonance at wavelengths of incident light that are between the wavelength of two different excitation lasers. By tuning the incident angle, any laser within a certain range of the excitation wavelength of the fluorescent dye can be used with the same sensor, with the same laser polarization. Fluorescent images of each dye can then be taken using a multi-laser confocal scanning detection instrument which has the ability to excite the PC surface with a selected angle of incidence, and the wavelength/angle combination that yields PCEF (photonic crystal enhanced fluorescence). In this disclosure, as one example of such a photonic crystal sensor we describe the design and characterization of a PC surface that is used to enhance the fluorescence from Cy-5, a dye excited by a $\lambda$=632.8 HeNe laser, and cyanine-3 (Cy-3), a dye excited by a $\lambda$=532 nm diode pumped solid state laser.

Thus, in one aspect, this invention relates to a photonic crystal sensor detection arrangement exhibiting resonant enhancement of multiple fluorophores. The sensor utilizes distinct resonant modes to enhance electric field stimulation of different dyes. Resonant coupling of laser excitation light to the photonic crystal surface is obtained for each wavelength at which the fluorophore is excited and at a distinct incident angle.

In one embodiment, the photonic crystal substrate is capable of enhancing excitation laser intensity for the wavelength range 532 nm to 660 nm, providing compatibility with a large variety of commonly used fluorescent dyes, such as Rhodamine, Texas Red, Cy-5 and Cy-3 dyes, and Alexa fluor 532 to 647, which are widely used in life science research, diagnostic testing, and environmental detection.

In one example of the invention, the sensor exhibits a 32× increase in fluorescent signal intensity for cyanine-5 conjugated strepavidin labeling, while a 25× increase was obtained for cyanine-3 conjugated streptavidin labeling, compared to detection of same fluorophores on an ordinary glass surface. The current device design improves the signal-to-noise ratio for detection of analytes tagged with multiple dyes at low concentration.

In one possible manufacturing method, the photonic crystals of this disclosure can be fabricated by a low cost replica molding method that can be performed uniformly over a large surface area. Alternatively, fabrication of the photonic crystal surface on a low auto-fluorescence quartz substrate is contemplated to further improve the signal-to-noise-ratio of multicolor fluorescence detection.

In another aspect, the invention can be considered as method of conducting an assay with a photonic crystal sensor, comprising the steps of: providing a photonic crystal sensor having a 1-D periodic grating structure and having fluorophores 1 and 2 deposited thereon, illuminating the sensor with a first laser emitting light at wavelength $\lambda 1$ at a first angle of incidence so as to produce enhanced electric field excitation of the first fluorophore; and illuminating the sensor with a second laser emitting light at wavelength $\lambda 2$ at a second angle of incidence so as to produce enhanced electric field excitation of the second fluorophore.

As an alternative to using two different lasers, a single tunable laser could be used. In this embodiment a method of conducting an assay with a photonic crystal sensor comprises the steps of: providing a photonic crystal sensor having a 1-D periodic grating structure and having fluorophores 1 and 2 deposited thereon, illuminating the sensor with a tunable laser emitting light at wavelength $\lambda 1$ at a first angle of incidence so as to produce enhanced electric field excitation of the first fluorophore; and illuminating the sensor with the tunable laser emitting light at wavelength λ2 at a second angle of incidence so as to produce enhanced electric field excitation of the second fluorophore.

In another embodiment, the photonic crystal can be designed for resonant coupling at two distinct laser wavelengths for two separate incident angles, as shown in FIG. 2. For each laser wavelength, multiple fluorophores may be selected with an absorption spectrum that overlaps with the excitation wavelength, but with different emission wavelengths. For example, a total of four fluorophores can be utilized for photonic crystal enhanced fluorescence at once using a combination of two laser wavelengths and two fluorescent dye molecules per laser. A potential application for this approach would be labeling each of the four nucleotides in DNA (A, G, C & T) or RNA (A, G, C, & U) with a different fluorophore, and for each fluorophore's emission to be enhanced when present on the surface of the photonic crystal. This approach can be used to enhance the fluorescent signal for DNA or RNA sequencing applications that utilize incorporation of one fluorescent dye molecule at a time to surface-immobilized DNA or RNA strands. In this case, a total of four fluorescent images of the photonic crystal surface would be gathered in sequence (two lasers, each matched to the adsorption spectrum of two different fluorescent dye molecules, with each laser illuminating the photonic crystal at the resonant coupling angle for the laser wavelength) to determine the locations on the photonic crystal surface that incorporated each fluorescent dye molecule. The locations of DNA or RNA binding may represent single molecules, or small clusters containing many molecules.

In one aspect, the invention can be considered a detection apparatus comprising, in combination: a photonic crystal sensor having a 1-D periodic grating structure designed with a single resonant wavelength that is between the wavelengths of at least two different excitation wavelengths of at least two different fluorescent dyes applied to the sensor surface, and one or more lasers emitting light at the excitation wavelengths, light from the lasers impinging on the photonic crystal sensor at an incident angle θ, wherein a tuning of the incident angle θ of light from the one or more lasers produces electric field enhancement of the fluorescence from the at least two different fluorescent dyes.

In another aspect, a method of conducting an assay with a photonic crystal sensor, is disclosed comprising the steps of (a) providing a photonic crystal sensor having a 1-D periodic grating structure and having fluorophores 1, 2, ... N deposited thereon where N is an integer greater than or equal to 3; illuminating the sensor with a first laser emitting light at wavelength λ1 at a angle of incidence so as to produce enhanced electric field excitation of the first fluorophore and the second fluorophore; and (c) illuminating the sensor with light from a second laser emitting light at wavelength λ2 at a angle of incidence so as to produce enhanced electric field excitation of the third fluorophore.

BRIEF DESCRIPTION OF THE DRAWINGS

FIG. 2. (b) is a plot of the simulated near field distribution at λ=532 nm and λ=633 nm, the plot generated using RCWA.

DETAILED DESCRIPTION

Figure 1A:
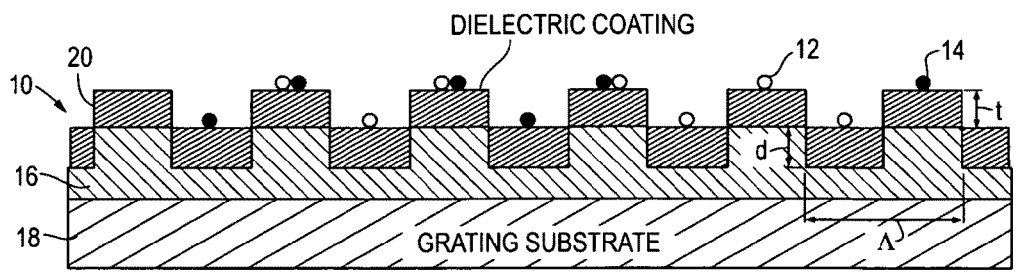
FIG. 1A is a cross-sectional diagram (not to scale) of a photonic crystal (PC) sensor exhibiting resonant enhancement of multiple fluorophores. The dimensions of the embodiment of FIG. 1 are as follows: Λ=360 nm, grating depth d=60 nm, SiO$_2$ thickness t$_{SiO2}$=120 nm, and TiO$_2$ thickness t$_{TiO2}$=160 nm. The grating width is 35% of the period.

In a first aspect, a photonic crystal sensor exhibiting resonant enhancement of multiple fluorophores is disclosed. The sensor device, which may be fabricated uniformly from plastic materials over a ~3×5 in$^2$ surface area by nanoreplica molding, utilizes two distinct resonant modes to enhance electric field stimulation of a first dye excited by a λ=632.8 nm laser (cyanine-5) and a second dye excited by a λ=532 nm laser (cyanine-3). Resonant coupling of the laser excitation to the photonic crystal surface is obtained for each wavelength at a distinct incident angle θ.

Compared to detection of a dye-labeled protein on an ordinary glass surface, the photonic crystal surface exhibited a 32× increase in fluorescent signal intensity for cyanine-5 conjugated strepavidin labeling, while a 25× increase was obtained for cyanine-3 conjugated streptavidin labeling. The photonic crystal is capable of amplifying the output of any fluorescent dye with an excitation wavelength in the 532 nm<λ<633 nm range by selection of an appropriate incident angle. The device is designed for biological assays that utilize multiple fluorescent dyes within a single imaged area, such as gene expression microarrays.

The present sensor can resonantly couple light from multiple excitation lasers—each at a distinct incident angle—to provide enhanced fluorescence for multiple dyes. In one embodiment, images of the fluorescence are generated by a camera. In particular, the fluorescent images of each dye can then be taken using a multi-laser confocal scanning detection instrument which has the ability to excite the PC surface with a selected angle of incidence, and the wavelength/angle combination that yields PCEF.

In this illustrated embodiment of FIG. 1, we describe the design and characterization of a PC (10) that is used to enhance the fluorescence from Cy-5 (12), a dye excited by a λ=632.8 HeNe laser and cyanine-3 (14) (Cy-3), a dye excited by a λ=532 nm diode pumped solid state laser.

A cross-sectional diagram (not to scale) of the PC surface is shown in FIG. 1. The one-dimensional (1-D) surface grating structure was formed in ultraviolet curable polymer (UVCP) (16) on a polyethylene-terephthalate (PET) (18) substrate by the nanoreplica molding technique. Nanoreplica molding of photonic crystal sensors is described in reference [17] and in the patent literature, therefore a detailed description is not necessary to the present discussion. The polymer grating surface (16) was coated with a high refractive index dielectric layer of $TiO_2$ (20) which functions as a wave confinement layer. Under broadband illumination, a highly efficient reflection represents a resonance at a specific wavelength and a specific angle. A simulation tool (DiffractMOD, RSoft Design Group) based on the rigorous coupled-wave analysis (RCWA) technique was used to design the 1-D surface PC structure. In order to support resonances at $\lambda=632.8$ nm and $\lambda=532$ nm concurrently, RCWA simulation results stipulated the use of a grating with a period of $\Lambda=360$ nm. Other device parameters include the grating depth of $d=25$ nm, $TiO_2$ thickness of $t_{TiO2}=100$ nm, UVCP refractive index of $n_{UVCP}=1.47$, and $TiO_2$ refractive index of $n_{TiO2}=2.35$. The transmission spectra were calculated by RCWA and the minimum transmissions (or maximum reflections) in the spectra were used to identify the resonant mode supported by the designed structure [18].

Figure 1B:
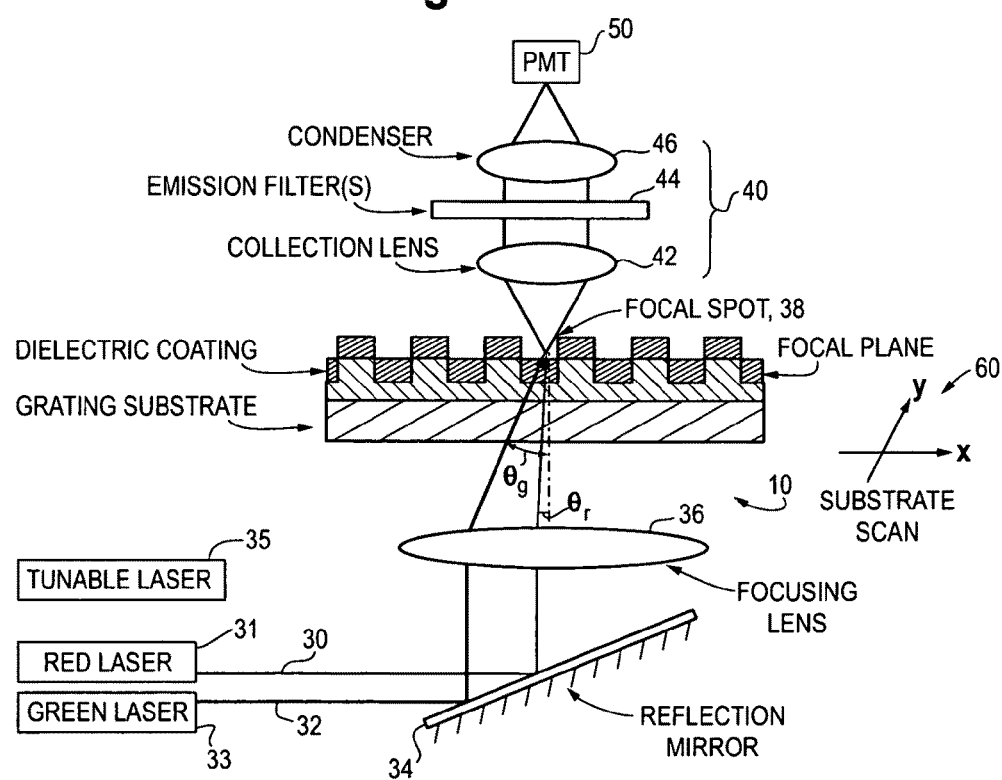
FIG. 1B is a illustration of an instrument used to illuminate the sensor of FIG. 1 and obtain images therefrom, e.g., using a photomultiplier tube (PMT) or digital camera. The instrument can for example take the form of a multi-laser confocal scanning instrument.

An instrument for illumination of the sensor is shown in FIG. 1B. The instrument includes two lasers 31 and 33 producing beams 30 and 32 at wavelengths $\lambda 1$ and $\lambda 2$, respectively which reflect off a mirror 34 to a focusing lens 36 which directs the laser light to the photonic crystal sensor 10. The angle of incidence of the red beam 30 is shown by the symbol $\theta_r$ and the angle of incidence of the green beam 32 is shown by the symbol $\theta_g$. The beams converge on a focal spot 38. The sensor 10 grating structure is designed to produce resonance at the wavelengths $\lambda 1$ and $\lambda 2$ and thus enhance the excitement of the fluorophores (FIG. 1A, at 12 and 14). The instrument includes collection optics 40 for collecting fluorescence and directing the fluorescence light to a photomultiplier tube 50 or alternatively a digital CCD camera. The collection optics 40 includes a collection lens 42, emission filter(s) 44 passing light at the emission wavelength of the fluorophores and a condenser 46. The sensor 10 sits on a scanning XY moveable stage, whereby the focal spot 38 can be moved in X and Y directions as indicated at 60 to thereby successively illuminate the entire sensor 10 surface.

The angle of incidence $\theta$ for the lasers 31 and 33 depends upon the location at which the laser light impinges on the focusing lens 36 as shown in FIG. 1B. This location can be changed by repositioning the lasers 31 and 33 in the instrument. Other ways of changing the angle of incidence may be performed, for example by moving or rotating the reflection mirror 34 or moving the location of the focusing lens 36.

Figure 2A:
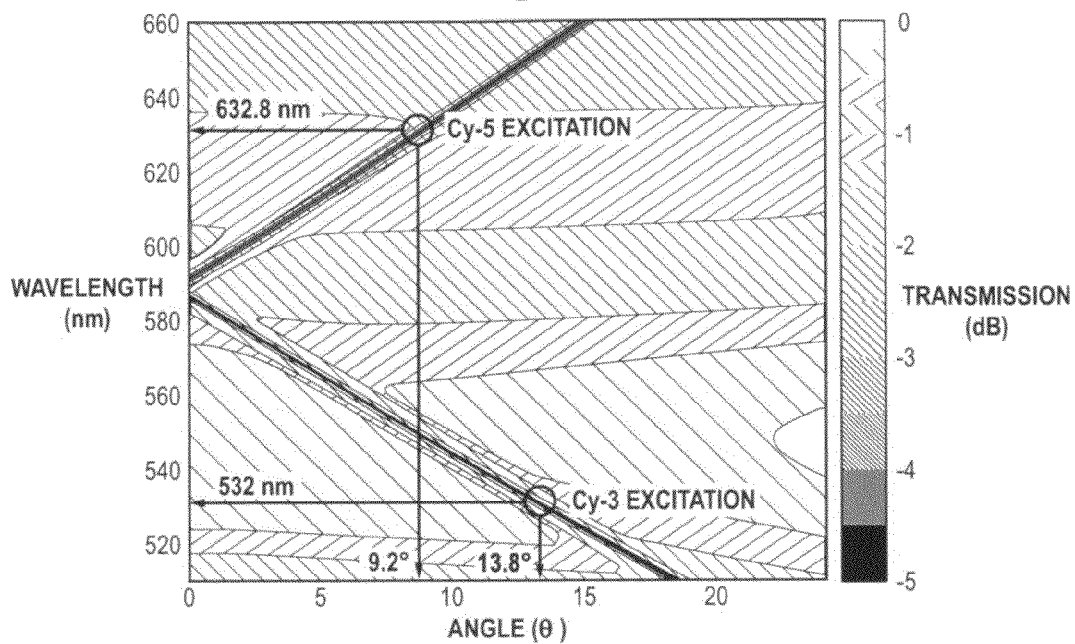
FIG. 2. (a) is a simulated dispersion diagram for the PC of FIG. 1 generated using RCWA (rigorous coupled-wave analysis). Resonance for the enhanced excitation for the TM mode is θ~9.2° for Cy-5 excitation and θ~13.8° for Cy-3 excitation.
Figure 2B:
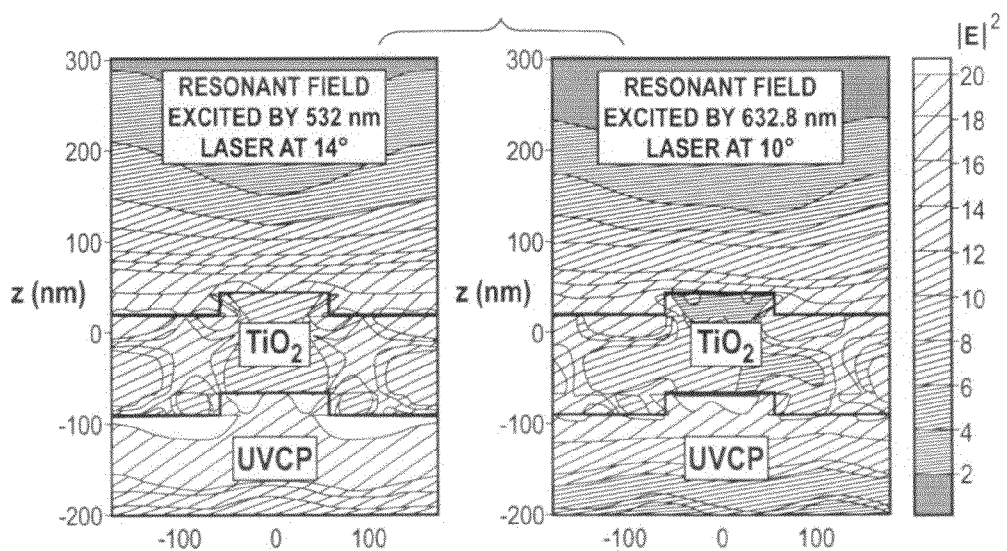

As shown in FIG. 2(a), a photonic band diagram for the structure shown in FIG. 1A was calculated for transverse magnetic (TM) modes in the 510 nm$<\lambda<$660 nm wavelength interval where the incident angle varied from $0°<\theta<20°$. From the photonic band diagram, a resonant angle of $\theta=13.8°$ corresponds to a resonant wavelength of $\lambda=532$ nm, while a resonant angle of $\theta=9.2°$ corresponds to a resonant wavelength of $\lambda=632.8$ nm. FIG. 2(b) shows the spatial distribution of the simulated near-field electric field intensity (normalized to the intensity of incident field) for the excitation of the resonant mode at $\lambda=532$ nm and $\lambda=632.8$ nm. The influence of the resonance phenomenon on the resulting near-fields is clearly manifested in the electric field intensity.

Figure 3:
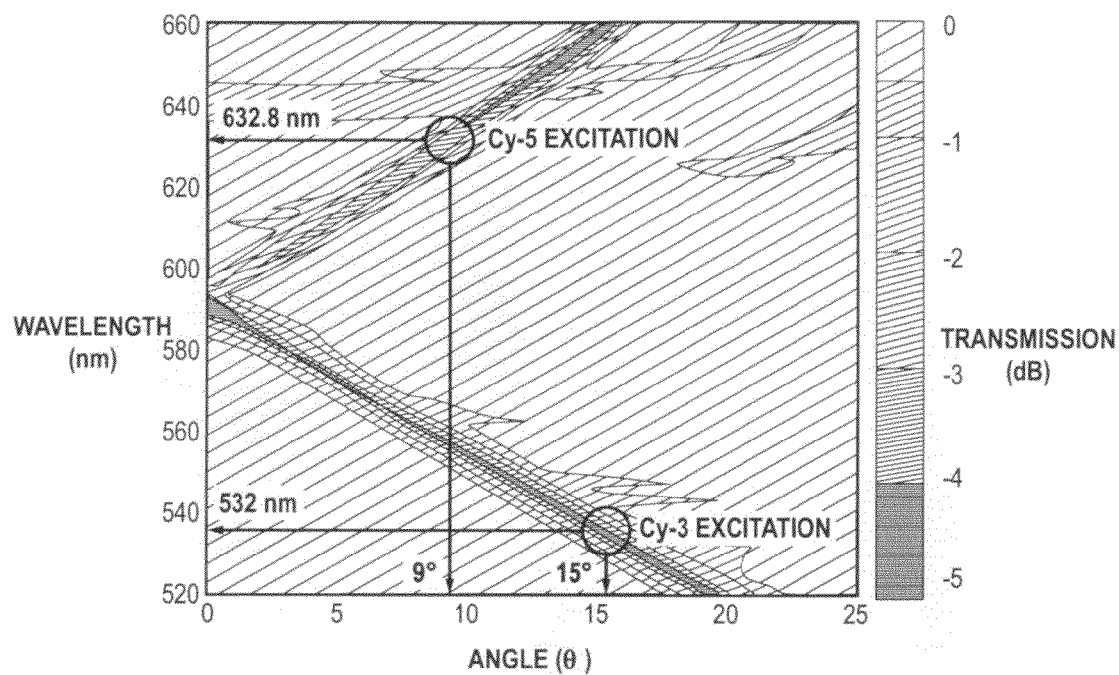
FIG. 3 is a measured dispersion diagram for the PC used in this study by RCWA (Rigorous Coupled Wave Analysis). Resonance for the enhanced excitation for the TM mode is θ~9° for Cy-5 excitation and θ~15° for Cy-3 excitation.

Fabrication of the sensor of FIG. 1A was carried out using a plastic-based nanoreplica molding process. Briefly, a silicon wafer with a negative surface volume image of the desired grating pattern was fabricated using deep-UV lithography and reactive ion etching. A liquid UVCP was sandwiched between a PET sheet and the silicon master wafer, and was subsequently cured using a high intensity UV lamp (Xenon, Inc). The hardened polymer grating adhered to the PET and was peeled away from the master, and the replica was cut and attached to a 1×3 inch microscope slide. A thin $SiO_2$ intermediate layer ($t_{SiO2}=80$ nm) on the grating surface 16 and below the dielectric coating layer 20 helps to reduce autofluorescence from the underlying polymer material. Following $SiO_2$ deposition, 120 nm of $TiO_2$ was sputtered by a RF sputtering system (PVD 75, Kurt Lesker). The photonic band diagram of the device was obtained by illuminating the device with collimated white light and measuring the transmitted spectrum with a spectrometer (USB 2000, Ocean Optics) as a function of incident angle. The consequent band diagram is shown in FIG. 3, which agrees well with the simulated band diagram shown in FIG. 2(a). As highlighted in FIG. 3, resonances for $\lambda=532$ nm and $\lambda=632.8$ modes lie at $\theta=15°$ and $\theta=9°$, respectively.

In order to demonstrate the fluorescence enhancement performance of the fabricated sensor, a detection experiment using a dye-labeled protein was carried out on the PC surface (10, FIG. 1) and a reference glass slide. Both the PC surface and the glass slide were pre-cleaned with $O_2$ plasma (TI Plasma) for 3 min. and functionalized by overnight incubation in an enclosed glass container with 5% 3-glycidoxypropyldimethylethoxysilane in dry toluene at 100° C. After incubation the silanized devices were cleaned by sonication in toluene, methanol and deionized (DI) water and then dried under a nitrogen stream. Cy-5 and Cy-3 conjugated streptavidin (GE Healthcare) at 50 μg/ml was spotted onto the slides as two separate arrays by a piezo dispenser (Piezorray, Perkin Elmer). After overnight incubation, the devices were washed by gently dipping them in a protein blocking buffer (Phosphate buffered saline at pH 7.4 with Kathon antimicrobial agent) solution for 60 sec. followed by DI water rinse. Fluorescent images of the spots were obtained using a commercially available confocal laser scanner (LS-Reloaded, Tecan) equipped with a $\lambda=632.8$ nm He—Ne laser and a $\lambda=532$ nm solid state laser. The angle of incidence of both lasers can be tuned from $\theta=0°$ to $\theta=25°$. The Cy-5 conjugated streptavidin and Cy-3 conjugated streptavidin spots were sequentially illuminated by TM-polarized $\lambda=632.8$ nm and $\lambda=532$ nm lasers with Cy-5 and Cy-3 emission filters ($\lambda=692\pm40$ nm; $\lambda=575\pm50$ nm). The measured images were analyzed by image processing software (ImageJ). The net fluorescence intensity was calculated by averaging spot intensities over the 16 replicate spots minus the local background intensity.

Figure 4A:
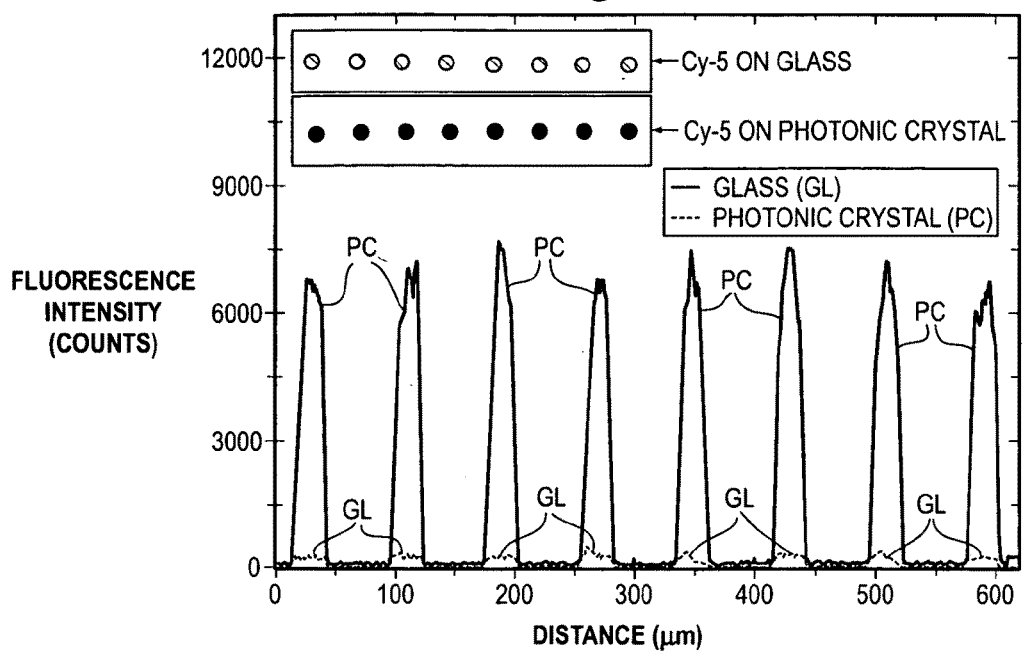
FIG. 4a is an intensity profile as a function of distance for a line of fluorescent image pixels profiling spots of Cy-5 conjugated streptavidin for both the glass slide and the PC under normal incidence illumination. The scanned images are shown in insets.
Figure 4B:
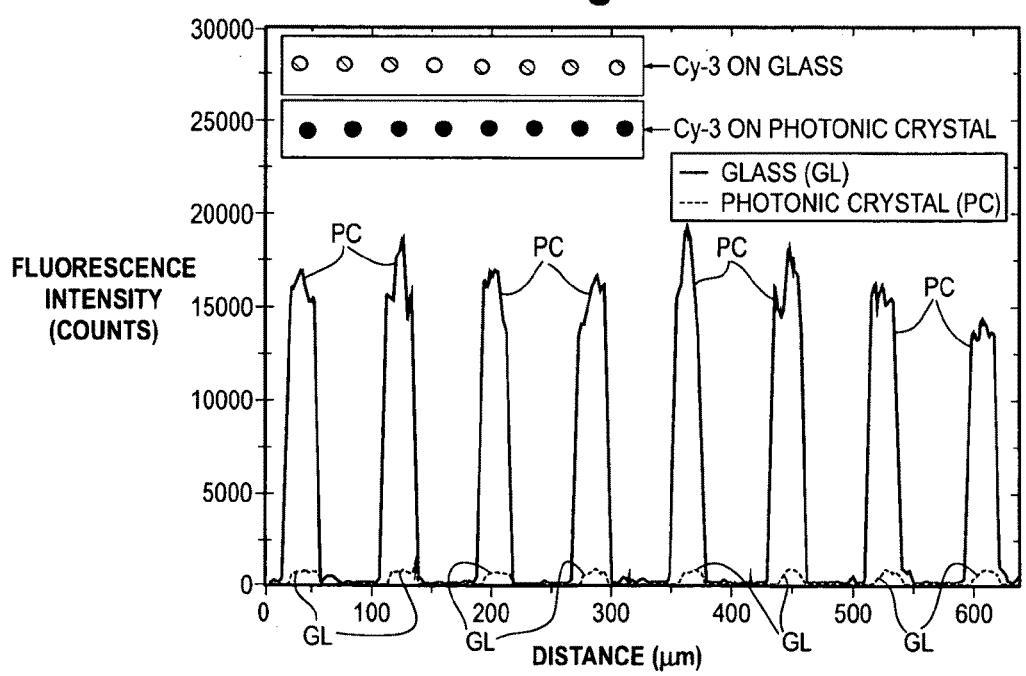
FIG. 4b. is an intensity profile as a function of distance for a line of fluorescent image pixels profiling spots of Cy-3 conjugated streptavidin for both the glass slide and the PC under normal incidence illumination. The scanned images are shown in insets.

The He—Ne laser at $\theta=15°$ was used to excite the Cy-5 conjugated streptavidin spots, which demonstrated an amplification of Cy-5 emission on the PC surface by a factor of 32 compared to the glass slides measured under same condition. Similarly, Cy-3 conjugated streptavidin spots were excited by the green laser at $\theta=9°$, which showed an enhancement by a factor of 25, compared to the glass surface. The scanned images from the PC and glass substrates are compared in the insets of FIG. 4(a-b) (images were plotted using the same color scale). Representative line profiles generated by extracting fluorescence intensities from a single line of pixels through 8 spots on the photonic crystal and glass images for both fluorophores is also shown in FIGS. 4(a) and 4(b). This profile clearly illustrates amplification of the emission signal from both fluorophores on the PC surface. The slight increase in background fluorescence in these images can be attributed to simultaneous enhancement of the fluorescent output originating from the polymer material used for nanoreplica molding the grating structure. The fluorescence images of the spots were taken at the small pinhole setting in the confocal laser scanner (LS-Reloaded, Tecan) with 10 μm image resolution. A PMT (photomultiplier tube) gain of 100 was used to scan SA-conjugated Cy-3 spots and a PMT gain of 130 was used to scan SA-conjugated Cy-5 spots.

In summary, a single PC surface has been used to enhance fluorescence emission from both Cy-5 and Cy-3 dyes. As understood by persons skilled in the art, the teachings can be extended to other fluorescent dyes, such as dyes selected from the group of fluorophores consisting of Rhodamine, Texas Red, Cy-5, Cy-3 dyes, and Alexa fluor 532 to 647.

The PC was fabricated by a low cost replica molding method that can be performed uniformly over a large surface area. To excite resonant modes at a desired wavelength, the excitation light needs to illuminate the PC 10 at a specific resonant angle by tuning the angle of incidence $\theta$. For the device demonstrated here, the resonance angle for $\lambda=632.8$ nm is $\lambda=9°$ while for $\theta=532$ nm, $\theta=15°$. Compared to a glass slide, the PC sensor exhibits an enhancement of 32× for Cy-5 and 25× for Cy-3. This particular PC is capable of PCEF for the wavelength range 532 nm<$\lambda$<660 nm, providing compatibility with a large variety of commonly used fluorescent dyes, such as Rhodamine, Texas Red, and Alexa fluor 532 to 647, which are widely used in life science research, diagnostic testing, and environmental detection.

Further Applications: Gene Expression Arrays and Two or More Fluorophores Per Laser.

In another embodiment, the photonic crystal sensor and detection arrangement of this disclosure can be designed for resonant coupling at two distinct laser incident (excitation) wavelengths for two separate incident angles, as shown in FIG. 2. For each laser incident wavelength, multiple fluorophores may be selected with an absorption spectrum that overlaps with the excitation wavelength of the laser, but each fluorophore has a different emission wavelength. For example, a total of four fluorophores can be utilized for photonic crystal enhanced fluorescence at once (or in sequence) using a combination of two laser wavelengths and two fluorescent dye molecules per laser.

A potential application for this approach would be labeling each of the four nucleotides in DNA (A, G, C & T) or RNA (A, G, C, & U) with a different fluorophore, and for the emission of each fluorophore to be enhanced when present on the surface of the photonic crystal. This approach can be used to enhance the fluorescent signal for DNA or RNA sequencing applications that utilize incorporation of one fluorescent dye molecule at a time to surface-immobilized DNA or RNA strands. In this case, a total of four fluorescent images of the photonic crystal surface would be gathered in sequence (two lasers, each matched to the adsorption spectrum of two different fluorescent dye molecules, with each laser illuminating the photonic crystal at the resonant coupling angle for the laser wavelength) to determine the locations on the photonic crystal surface that incorporated each fluorescent dye molecule. The locations of DNA or RNA binding may represent single molecules, or small clusters containing many molecules.

Thus, in one further aspect a method of conducting an assay with a photonic crystal sensor is contemplated, comprising the steps of: (a) providing a photonic crystal sensor having a 1-D periodic grating structure and having fluorophores 1, 2, . . . N deposited thereon where N is an integer greater than or equal to 3; (b) illuminating the sensor with a first laser emitting light at wavelength $\lambda 1$ at a angle of incidence so as to produce enhanced electric field excitation of the first fluorophore and the second fluorophore; and (c) illuminating the sensor with light from a second laser emitting light at wavelength $\lambda 2$ at a angle of incidence so as to produce enhanced electric field excitation of the third fluorophore. In one variation of this method, wherein N=4 and the method further comprises the step (d) illuminating the sensor with light from the second laser so as to produce enhanced electric field excitation of the fourth fluorophore. As noted above, in one embodiment the assay is in the form of a gene expression assay and the fluorophores are bound to nucleotides of DNA or RNA. The method may also be performed using a imaging step, and in particular imaging the photonic crystal sensor during excitation of the 1 . . . N fluorophores.

In another embodiment, a photonic crystal sensor and detection arrangement is contemplated comprising, in combination: a photonic crystal sensor having a 1-D periodic grating structure and having fluorophores 1, 2, 3 and 4 deposited thereon, an instrument having first and second lasers emitting light at wavelengths $\lambda 1$ and $\lambda 2$, respectively, wavelength $\lambda 1$ selected to excite the fluorophores 1 and 2, respectively and wavelength $\lambda 2$ selected to excite the fluorophores 3 and 4, respectively; wherein the sensor produces a resonance for incident radiation at wavelengths between $\lambda 1$ and $\lambda 2$, inclusive, within a given range of angles of incidence; wherein the angle of incidence $\theta 1$ of the first laser is selected so as to produce enhanced electric field stimulation of the fluorophores 1 and 2; and wherein the angle of incidence $\theta 2$ of the second laser is selected so as to produce enhanced electric field stimulation of the fluorophores 3 and 4.

REFERENCES

The following references are incorporated by reference herein.
1. Lakowicz, J. R., *Principles of Fluorescence Spectroscopy*. 3 ed. 2006: Springer. 954.
2. Geddes, C. D. and J. R. Lakowicz, *Metal-Enhanced Fluorescence*. Journal of Fluorescence, 2002. 12(2): p. 121-129.
3. Moal, E. L., et al., *Enhanced fluorescence cell imaging with metal-coated slides*. Biophysical Journal, 2007. 92: p. 2150-2161.
4. Estrada, L. C., et al., *Small volume excitation and enhancement of dye fluorescence on a 2D photonic crystal surface*. Optics Express, 2010. 18(4): p. 3693-3698.
5. Wu, H.-Y., et al., *Magnification of photonic crystal fluorescence enhancement via TM resonance excitation and TE resonance extraction on a dielectric nanorod surface*. Nanotechnology, 2010. 21: p. 7.
6. Kinkhabwala, A., et al., *Large single-molecule fluorescence enhancements produced by a bowtie nanoantenna*. Nature Photonics, 2009. 3: p. 4.
7. Lakowicz, J. R., *Radiative Decay Engineering: Biophysical and Biomedical Applications*. Analytical Biochemistry, 2001. 298: p. 1-24.
8. Fan, S. and J. D. Joannopoulos, *Analysis of guided resonances in photonic crystal slabs*. Physical Review B, 2002. 65: p. 235112.
9. Willets, K. A. and R. P. V. Duyne, *Localized Surface Plasmon Resonance Spectroscopy and Sensing*. Annual Review of Physical Chemistry, 2006. 58: p. 30.
10. Anger, P., P. Bharadwaj, and L. Novotny, *Enhancement and Quenching of Single-Molecule Fluorescence*. Physical Review Letter, 2006. 96(11): p. 4.
11. Ganesh, N., et al., *Leaky-mode assisted fluorescence extraction: application to fluorescence enhancement biosensors*. Optics Express, 2008. 16(26): p. 21626-21640.
12. Mathias, P. C., et al., *Graded Wavelength One-Dimensional Photonic Crystal Reveals Spectral Characteristics of Enhanced Fluorescence*. Journal of Applied Physics, 2008. 103: p. 094320.

13. Mathias, P. C., H.-Y. Wu, and B. T. Cunningham, *Employing two distinct photonic crystal resonances for improved fluorescence enhancement.* Applied Physics Letters, 2009. 95(2): p. 3.
14. Budach, W., et al., *Generation of transducers for fluorescence-based microarrays with enhanced sensitivity and their application for gene expression profiling.* Analytical Chemistry, 2003. 75: p. 2571-2577.
15. Che, D., Y. Bao, and U. R. Mueller, *Novel surface and multicolor charge coupled device-based fluorescent imaging system for DNA microarrays.* Journal of Biomedical Optics, 2001. 6(4): p. 450-456.
16. Ganesh, N. and B. T. Cunningham, *Photonic Crystal Near UV Reflectance Filters Fabricated by Nano Replica Molding.* Applied Physics Letters, 2006. 88(7): p. 071110-071113.
17. Block, I. D., L. L. Chan, and B. T. Cunningham, *Large-Area submicron replica molding of porous low-k dielectric films and application to photonic crystal biosensor fabrication.* Microelectronic Engineering, 2007. 84(4): p. 603-608.
18. Ganesh, N., et al., *Enhanced fluorescence emission from quantum dots on a photonic crystal surface.* Nature Nanotechnology, 2007. 2: p. 515-520.

We claim:

1. Detection apparatus comprising, in combination:
 a photonic crystal sensor having a 1-D periodic grating structure designed with a single resonant wavelength that is between the wavelengths of at least two different excitation wavelengths of at least two different fluorescent dyes applied to the sensor surface, and
 one or more lasers emitting light at the excitation wavelengths, light from the lasers impinging on the photonic crystal sensor at an incident angle $\theta$,
 wherein a tuning of the incident angle $\theta$ of light from the one or more lasers produces electric field enhancement of the fluorescence from the at least two different fluorescent dyes.

2. The apparatus of claim 1, wherein the lasers emit light at a wavelength of between 530 and 660 nanometers.

3. The apparatus of claim 1, wherein the sensor grating structure has a period $\Lambda$ of between 350-400 nm, and a grating depth d of between 20 and 100 nm.

4. The apparatus of claim 1, wherein at least one of the fluorescent dyes are selected from the group of fluorophores consisting of Rhodamine, Texas Red, Cy-5, Cy-3 dyes, and Alexa fluor 532 to 647.

5. A photonic crystal and instrument combination, comprising:
 a photonic crystal sensor having a 1-D periodic grating structure and having fluorophores 1 and 2 deposited thereon,
 an instrument having first and second lasers emitting light at wavelengths $\lambda 1$ and $\lambda 2$, respectively, wavelengths $\lambda 1$ and $\lambda 2$ selected to excite the fluorophores 1 and 2, respectively;
 wherein the sensor produces a resonance for incident radiation at wavelengths between $\lambda 1$ and $\lambda 2$, inclusive within a given range of angles of incidence, and
 wherein the angle of incidence $\theta$ of the first and second lasers is selected so as to produce enhanced electric field stimulation of the fluorophores 1 and 2.

6. The sensor and instrument combination of claim 5, wherein the instrument includes a focusing lens and wherein the angle of incidence $\theta$ is selected by changing the orientation of the first and second lasers relative to the focusing lens and thereby changing the location where laser light intersects the focusing lens.

7. The sensor and instrument combination of claim 5, further comprising an imaging device generating images of the sensor under conditions of the enhanced electric field stimulation of the fluorophores 1 or 2 or both.

8. A photonic crystal and instrument combination, comprising:
 a photonic crystal sensor having a 1-D periodic grating structure and having fluorophores 1 and 2 deposited thereon,
 a detection instrument having a tunable laser emitting light at wavelengths $\lambda 1$ and $\lambda 2$, wavelengths $\lambda 1$ and $\lambda 2$ selected to excite the fluorophores 1 and 2, respectively;
 wherein the sensor produces a resonance for incident radiation at a wavelength between $\lambda 1$ and $\lambda 2$ within a given range of incident angles, and
 wherein the angle of incidence of light from tunable laser onto the sensor is changed to angles of incidence $\theta 1$ and $\theta 2$ so as to produce enhanced electric field stimulation of the fluorophores 1 and 2 at wavelengths $\lambda 1$ and $\lambda 2$, respectively.

9. The sensor and instrument combination of claim 8, wherein the instrument includes a focusing lens and wherein the angle of incidence $\theta$ is selected by changing the orientation of the tunable laser relative to the focusing lens and thereby changing the location where laser light intersects the focusing lens.

10. The sensor and instrument combination of claim 8, further comprising an imaging device generating images of the sensor under conditions of the enhanced electric field stimulation of the fluorophores 1 or 2.

11. A method of conducting an assay with a photonic crystal sensor, comprising the steps of:
 providing a photonic crystal sensor having a 1-D periodic grating structure and having fluorophores 1 and 2 deposited thereon,
 illuminating the sensor with a first laser emitting light at wavelength $\lambda 1$ at a first angle of incidence $\theta 1$ so as to produce enhanced electric field excitation of the first fluorophore;
 illuminating the sensor with a second laser emitting light at wavelength $\lambda 2$ at a second angle of incidence $\theta 2$ so as to produce enhanced electric field excitation of the second fluorophore.

12. The method of claim 11, further comprising the steps of: generating an image of the sensor during the enhanced electric field excitation of the first and second fluorophores.

13. The method of claim 11, wherein the assay comprises a gene expression assay.

14. The method of claim 11 wherein fluorophore 1 and fluorophore 2 are excited by light at a wavelength between 530 and 660 nm.

15. The method of claim 11, wherein fluorophore 1 or fluorophore 2 is selected from the group of fluorophores consisting of Rhodamine, Texas Red, Cy-5, Cy-3 dyes, and Alexa fluor 532 to 647.

16. A method of conducting an assay with a photonic crystal sensor, comprising the steps of:
 providing a photonic crystal sensor having a 1-D periodic grating structure and having fluorophores 1 and 2 deposited thereon,
 illuminating the sensor with a tunable laser emitting light at wavelength $\lambda 1$ at a first angle of incidence so as to produce enhanced electric field excitation of the first fluorophore;

illuminating the sensor with the tunable laser emitting light at wavelength λ2 at a second angle of incidence so as to produce enhanced electric field excitation of the second fluorophore.

17. The method of claim 16, further comprising the steps of generating images of the sensor during the enhanced electric field excitation of the first and second fluorophores.

18. The method of claim 16, wherein the assay comprises a gene expression assay.

19. The method of claim 16, wherein fluorophore 1 and fluorophore 2 are excited by light at a wavelength between 530 and 660 nm.

20. The method of claim 16, wherein fluorophore 1 or fluorophore 2 is selected from the group of fluorophores consisting of Rhodamine, Texas Red, Cy-5, Cy-3 dyes, and Alexa fluor 532 to 647.

21. A method of conducting an assay with a photonic crystal sensor, comprising the steps of: (a) providing a photonic crystal sensor having a 1-D periodic grating structure and having fluorophores 1, 2, . . . N deposited thereon where N is an integer greater than or equal to 3;
  (b) illuminating the sensor with a first laser emitting light at wavelength λ1 at an angle of incidence so as to produce enhanced electric field excitation of the first fluorophore and the second fluorophore; and
  (c) illuminating the sensor with light from a second laser emitting light at wavelength λ2 at an angle of incidence so as to produce enhanced electric field excitation of the third fluorophore.

22. The method of claim 21, wherein N=4 and the method further comprises the step (d) illuminating the sensor with light from the second laser so as to produce enhanced electric field excitation of the fourth fluorophore.

23. The method of claim 22, wherein the fluorophores are bound to nucleotides of DNA or RNA.

24. The method of claim 23, further comprising the step of imaging the photonic crystal sensor during the performing of steps (b), (c), and (d).

25. A photonic crystal sensor and detection arrangement comprising, in combination:
  a photonic crystal sensor having a 1-D periodic grating structure and having fluorophores 1, 2, 3 and 4 deposited thereon,
  an instrument having first and second lasers emitting light at wavelengths λ1 and λ2, respectively, wavelength a λ1 selected to excite the fluorophores 1 and 2, respectively and wavelength λ2 selected to excite the fluorophores 3 and 4, respectively;
  wherein the sensor produces a resonance for incident radiation at wavelengths between λ1 and λ2, inclusive, within a given range of angles of incidence;
  wherein the angle of incidence θ1 of the first laser is selected so as to produce enhanced electric field stimulation of the fluorophores 1 and 2; and
  wherein the angle of incidence θ2 of the second laser is selected so as to produce enhanced electric field stimulation of the fluorophores 3 and 4.

* * * * *